(12) United States Patent
Marruchella et al.

(10) Patent No.: US 11,672,255 B2
(45) Date of Patent: Jun. 13, 2023

(54) METHOD FOR EVALUATING A HEALTH STATE OF AN ANATOMICAL ELEMENT, RELATED EVALUATION DEVICE AND RELATED EVALUATION SYSTEM

(71) Applicant: FARM4TRADE S.R.L., Chieti (IT)

(72) Inventors: Giuseppe Marruchella, Chieti (IT); Luca Bergamini, Chieti (IT); Andrea Capobianco Dondona, Chieti (IT); Ercole Del Negro, Chieti (IT); Francesco Di Tondo, Chieti (IT); Angelo Porrello, Chieti (IT); Simone Calderara, Chieti (IT)

(73) Assignee: FARM4TRADE S.R.L., Chieti (IT)

( * ) Notice: Subject to any disclaimer, the term of this patent is extended or adjusted under 35 U.S.C. 154(b) by 346 days.

(21) Appl. No.: 17/009,973

(22) Filed: Sep. 2, 2020

(65) Prior Publication Data
US 2021/0068404 A1    Mar. 11, 2021

(30) Foreign Application Priority Data
Sep. 9, 2019   (IT) .......................... 102019000015893

(51) Int. Cl.
    *A22B 5/00*      (2006.01)
    *G06N 20/00*     (2019.01)
    (Continued)

(52) U.S. Cl.
    CPC ............ *A22B 5/007* (2013.01); *A22C 17/008* (2013.01); *G01N 33/12* (2013.01); *G06N 20/00* (2019.01);
    (Continued)

(58) Field of Classification Search
    None
    See application file for complete search history.

(56) References Cited

U.S. PATENT DOCUMENTS

| | | | |
|---|---|---|---|
| 2009/0309960 A1* | 12/2009 | Park | G01J 3/0272 348/61 |
| 2016/0343120 A1* | 11/2016 | Johnson | G06Q 10/087 |
| 2020/0027207 A1* | 1/2020 | Zhang | G06K 9/6247 |

FOREIGN PATENT DOCUMENTS

| | | |
|---|---|---|
| WO | WO 92/00523 | 1/1992 |
| WO | WO 2018/186796 | 10/2018 |

OTHER PUBLICATIONS

Bergamini et al ("Segmentation Guided Scoring of Pathological Lesions in Swine Through CNNs", New Trends in Image Analysis and Processing—ICIAP 2019, Sep. 2, 2019, pp. 352-360, retrieved from the Internet on Oct. 4, 2022 (Year: 2019).*

(Continued)

*Primary Examiner* — Leon Viet Q Nguyen
(74) *Attorney, Agent, or Firm* — Leason Ellis LLP

(57) ABSTRACT

A method for evaluating (50) the health state of an anatomical element of an animal in a slaughtering plant provided with an image acquisition device. The evaluation method comprises the steps of: verifying the presence of the anatomical element; acquiring the image of the anatomical element; processing (S4) the image of the anatomical element through Deep Learning techniques, generating a lesion image representing lesioned portions of the anatomical element, and a number of processed images, each representing a corresponding non-lesioned anatomical area of the animal; for each of the lesioned portions and for each of the non-lesioned anatomical areas, determining a corresponding quantity indicative of the probability that said lesioned portion corresponds to said non-lesioned anatomical area; determining a score indicative of the health state of the anatomical element, depending on the determined quantities.

13 Claims, 5 Drawing Sheets

(51) Int. Cl.
 *A22C 17/00* (2006.01)
 *G01N 33/12* (2006.01)
 *G06T 7/00* (2017.01)

(52) U.S. Cl.
 CPC .......... *G06T 7/0004* (2013.01); *G06T 7/0014* (2013.01); *G06T 2207/20081* (2013.01); *G06T 2207/20084* (2013.01); *G06T 2207/30096* (2013.01); *G06T 2207/30128* (2013.01)

(56) References Cited

OTHER PUBLICATIONS

Bergamini Luca et al: "Segmentation Guided Scoring of Pathological Lesions in Swine Through CNNs", Sep. 2, 2019 (Sep. 2, 2019), ROBOCUP 2008: ROBOCUP 2008: Robot Soccer World Cup XII; [Lecture Notes in Computer Science; Lect.Notes Computer], Springer International Publishing, Cham, pp. 352-360, XP047519631, ISBN: 978-3-319-10403-4 [retrieved on Sep. 2, 2019] * abstract * * p. 354 * * Section 2 * * Section 3 * * Section 4 * * figures 1,3 *.

* cited by examiner

METHOD FOR EVALUATING A HEALTH STATE OF AN ANATOMICAL ELEMENT, RELATED EVALUATION DEVICE AND RELATED EVALUATION SYSTEM

CROSS-REFERENCE TO RELATED APPLICATIONS

This Patent Application claims priority from Italian Patent Application No. 102019000015893 filed on Sep. 9, 2019, the entire disclosure of which is incorporated herein by reference.

TECHNICAL FIELD

The present invention relates to an evaluation method, a related evaluation device, and a related evaluation system.

BACKGROUND ART

The need for identifying lesions present on portions of animal carcasses of food-producing animals (such as pigs, cattle, poultry) at the slaughterhouse (for example, on half carcasses or on organs of slaughtered animals) is known. In particular, the need for having, in real time, a systematic scan (identification and scoring) of all half carcasses and/or organs which is simultaneously efficient, standardized in compliance with the applicable law or according to otherwise defined parameters, as well as economically more advantageous than the current performed evaluation systems is known.

In fact, currently such detection activities of carcass lesions are visually performed by skilled and trained staff. For example, such activity is performed manually at present by a certified and high-skilled operator, usually having many years of experience, who personally performs all operations in difficult environmental conditions, sometimes risky and limited by the organization of the areas and work flow. Both inspection (official inspections by the health authorities) and health evaluations (evaluations by veterinarians working for the owner of the slaughtered animals) are thus performed personally by the operator through the visual and/or tactile analysis of the carcasses and organs.

Consequently, in the current slaughtering practices, only a part representative of the slaughtered animals is usually subject to such evaluations, based on the needs and availability of trained staff. Such evaluations are indeed particularly expensive both in terms of time spent and staff costs. In fact, this makes it impossible to systematically perform these assessments, particularly the scoring of lesions.

These health evaluations have a mainly productive relevance and are carried out by the operator (usually company or contract veterinarians) who examines organs and/or apparatuses in which it is possible to detect the lesions indicative of acute or chronic diseases contracted on the farm, and whose outcomes are easily visible on the organs or half carcass. This evaluation is carried out by scoring the carcasses or lesions in order to assess in a standard way the seriousness and/or extent thereof. This allows for the data to be compared both within the same stock farm and between different stock farms.

In modern zootechnics, the slaughterhouse represents a privileged observation point to evaluate the health state of food-producing animal populations, as well as to verify the effectiveness of the measures implemented for controlling certain stock farm diseases. This applies especially to pigs because the short productive cycle of the pig causes the lesions to be still visible and quantifiable during slaughter.

In detail, several methods which can be implemented by the operator to quantitatively evaluate the lesions at the slaughterhouse are known. The above methods must meet some fundamental requirements, regardless of the diseases examined: they must be carried out quickly so as not to interfere with the other operations in the slaughter chain; they must be objective, easily standardizable, reproducible and repeatable; they must provide easy-to-interpret and suitable data for statistical processing.

To date, a number of methods for scoring lesions have been developed, with special attention to the respiratory diseases (such as pneumonia and pleurites) in light of their impact on the profitability of the stock farm. Indeed, pleurites, especially those with chronic evolution, are commonly found in slaughtered pigs and can be caused by a number of pathogenic bacteria, all of great relevance in modern pig farm: *Actinobacillus pleuropneumoniae, Haemophilus parasuis, Streptococcus suis, Pasteurella multocida, Mycoplasma hyorhinis*. The association between the presence of pleural lesions in slaughtered pigs and the profitability of the same animals is widely documented (for example, daily weight gain and conversion index of the foodstuff). Moreover, the same lesions, like those in the lungs, are also related to the use of antimicrobials during breeding. This explains the attention which has always been paid to the assessment and scoring of pleurites in pigs.

The main disadvantages of the currently known scoring systems are:
- they are performed by humans and therefore subject to errors such as for example: subjective judgment, fatigue, and oversight;
- sample-based or partial inspection of slaughtered animal batches. On average, no more than 10-20% of the total slaughtered animals are inspected for evaluating the presence of certain lesions and many small slaughterhouses do not carry out any evaluation of the carcasses. This is largely due to the high costs, but also to the impossibility to find a sufficient number of evaluators on the market for all the structures present on the territory;
- insufficient standardization when scoring the seriousness and/or extent of the lesions;
- the process of data collection and analysis, by a human operator, is strongly influenced, and often penalized, by the conditions of the areas and by the organization of the work flow;
- the collection of data/information at the slaughterhouse is often carried out by recording the observations with a dictaphone or alternatively by taking paper notes. This requires additional hours of work outside the slaughterhouse to allow the transfer of the data in digital format in order to allow the analysis and sharing thereof.

DISCLOSURE OF INVENTION

The object of the present invention is to provide an evaluation method, a related evaluation device and a related evaluation system which overcome the above disadvantages in an efficient and cost-effective way.

In particular, the present invention allows developing a system and an automatic evaluation method of the lesions on an anatomical element (according to different embodiments, the carcass or portions thereof, such as organs) of an animal at the slaughterhouse. The detection of lesions is applicable, as better described below, to all diseases which can be identified through the image analysis and for which a scoring system has already possibly been developed or can be developed capable of providing an index of the seriousness, and therefore measurability, of the problem. Among the diseases that best match these characteristics we can include, in a non-limiting way, pleurites, pneumonias, parasitic hepatitises, skin lesions.

According to the present invention, an evaluation method, a related evaluation device and a related evaluation system are realized, as defined in the appended claims.

BRIEF DESCRIPTION OF THE DRAWINGS

For a better understanding of the present invention, a preferred embodiment is now described, purely by way of a non-limiting example, referring to the attached drawings, wherein.

BEST MODE FOR CARRYING OUT THE INVENTION

In the following description, common elements in the different embodiments have been referred to with the same reference numbers.

The present invention relates to an evaluation device (hereinafter referred to as reference number 45' in FIG. 2 and with reference number 45" in FIG. 3), and related evaluation system (hereinafter referred to as reference number 30' in FIG. 2 and reference number 30" in FIG. 3), for evaluating the health state of anatomical elements in slaughtering plants. The evaluation device 45', 45" (and therefore the evaluation system 30', 30") is adapted to perform, in use, an evaluation method (referred to as reference number 50 in FIG. 4).

Figure 1:
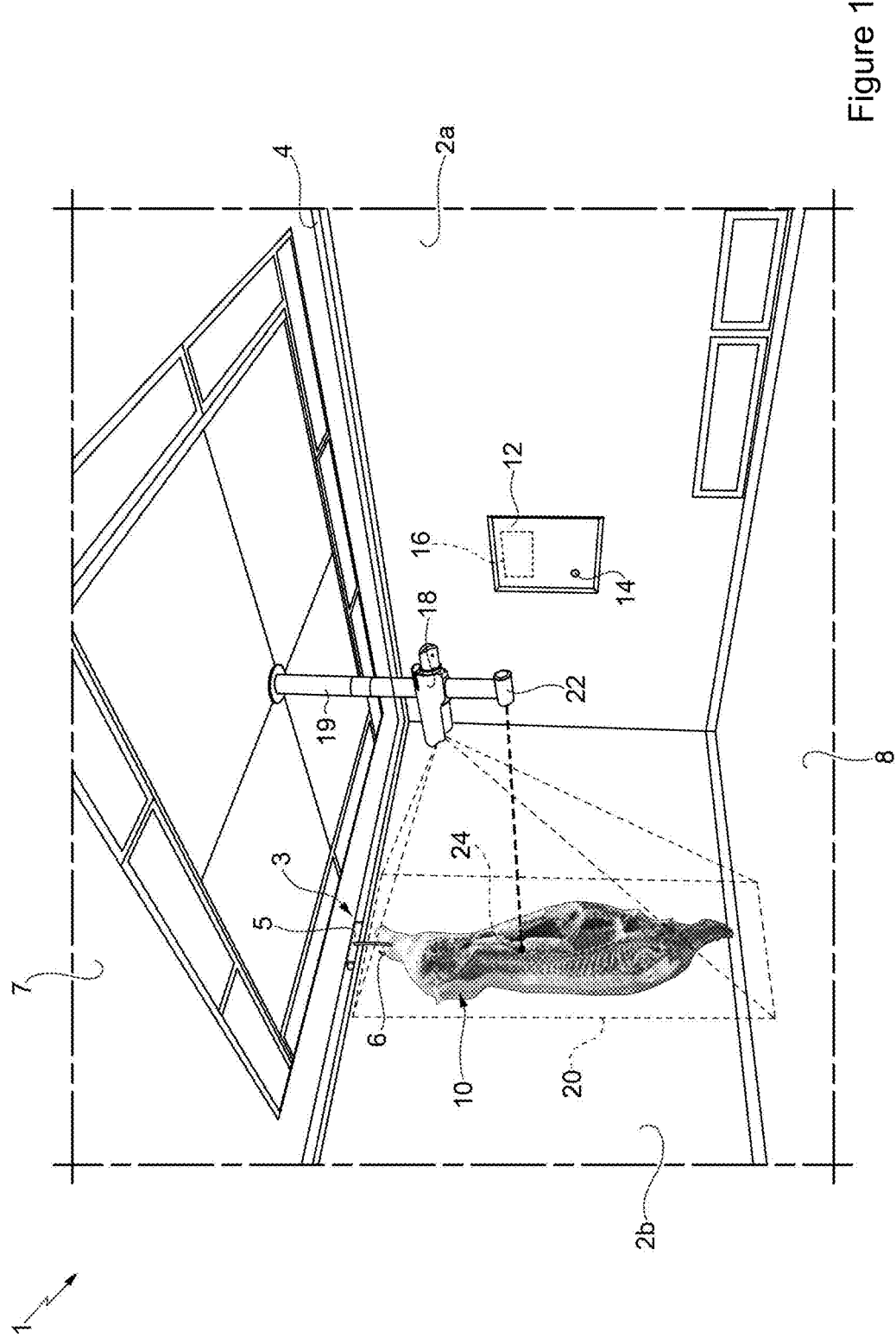
FIG. 1 is a schematic perspective view of a slaughtering plant according to an embodiment.

FIG. 1 shows a slaughtering plant 1 of a known kind according to an embodiment of the present invention. In particular, the slaughtering plant 1 of FIG. 1 is defined and externally delimited by a plurality of side walls 2 (in FIG. 1, a first and a second side wall 2a, 2b), a ceiling 7 and a floor 8.

In the embodiment described by way of example, the first side wall 2a houses a control panel 12 of a known kind which includes a control device 16 (comprising for example a dedicated controller, or a computer of a known kind having a control unit, etc.) and an on/off button 14 (as a bistable switch) operatively connected to the control device 16. The ceiling 7 houses a guide device 3 of a known kind which comprises a slide guide 4 and at least a slide 5. The slide guide 4 is integral with the ceiling 7 and comprises at least one straight path (in FIG. 1, two straight paths mutually connected by an angle joint element). The slide 5 is physically connected to the slide guide 4 so as to slide in the slide guide 4 along its path. Furthermore, a hook 6 is physically connected to and integral with the slide 5 and configured to hook and support an anatomical element 10 (in FIG. 1, a half carcass, hereinafter referred to as carcass 10; according to a different embodiment, the anatomical element 10 includes one or more portions of the carcass 10, for example one or more organs) of a food-producing animal (for example, a pig, a cow, etc.). The carcass 10 is therefore moved, by the staff or in an automated way, through the slaughtering plant 1 through the guide device 3. The slaughtering plant 1 also houses at least one image acquisition device 18, 22 including a camera 18 physically connected to (in detail, integral with) the ceiling 7 via a support 19 and adapted, in use, for monitoring at least one specific area of the slaughtering plant 1. In particular, the camera 18 is arranged in the slaughtering plant 1 so as to acquire an image of an observation area 20 which, in the embodiment described by way of example, corresponds to at least a portion of the second side wall 2b. In detail, when the carcass 10 is moved in the slaughtering plant 1 through the guide device 3, it passes through the observation area 20. Furthermore, the image acquisition device 18, 22 includes at least one sensor 22 (of a known kind, such as a photocell, or a sensor based on laser technology, or an acoustic sensor) adapted for detecting the passage of the carcass 10 through the observation area 20. In the embodiment described by way of example, the sensor 22 is attached to the support 19 and measures a detection zone 24 within the observation area 20. Both the sensor 22 and the camera 18 are operatively connected to, and driven by, the control device 16. In use, when the carcass 10 passes at the detection zone 24, the sensor 22 detects the carcass 10 in a known manner, and the camera 18 acquires the image of the observation area 20. Therefore, the image shows the carcass 10.

Figure 2:
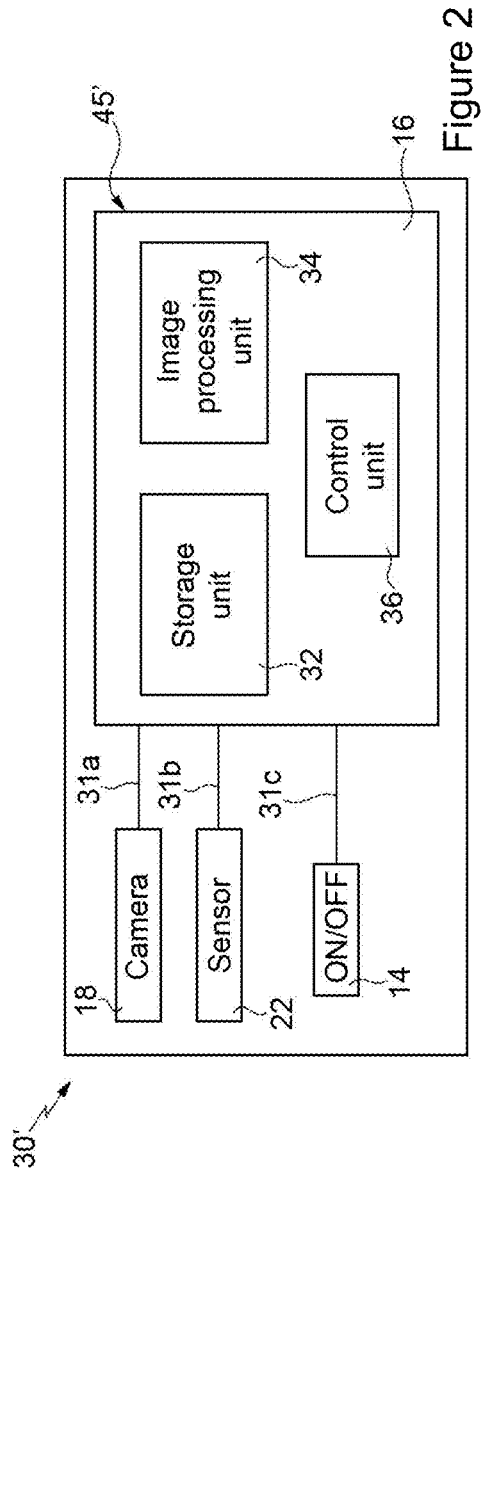
FIG. 2 schematically shows an evaluation system according to an embodiment of the present invention.

Referring to FIG. 2, the evaluation system according to an embodiment of the present invention is shown schematically (evaluation system 30'), wherein the evaluation method 50 is performed locally (on site in the slaughtering plant 1). In particular, the evaluation system 30' comprises the control device 16, the camera 18, the sensor 22, and the on/off button 14. The camera 18, the sensor 22 and the on/off button 14 can be electrically coupled to the control device 16 through first, second, and third electrical connections 31a, 31b, 31c, respectively (alternatively, through respective electromagnetic connections, such as wireless connections). The control device 16 comprises: a control unit 36 (such as a microprocessor or dedicated controller) configured to control and manage, in a known and therefore not described manner, the camera 18, the sensor 22, and the on/off button 14, acquiring therefrom, in use, respective output signals, processing such output signals and generating respective control input signals; a storage unit 32 including at least one known kind of memory (for example, a "Random Access Memory", RAM) and operatively coupled to the control unit 36; and a first image processing unit 34 operatively coupled to the control unit 36. In particular, in the present embodiment, the first image processing unit 34 is a local server (i.e., located in the slaughtering plant 1), a graphics processing unit (GPU), a central processing unit (CPU), a processor for mobile devices, or a dedicated processor or microprocessor. The first image processing unit 34 performs, in use, the evaluation method 50, as better described below. Furthermore, in the present embodiment, the evaluation device 45' is the control device 16.

Figure 3:
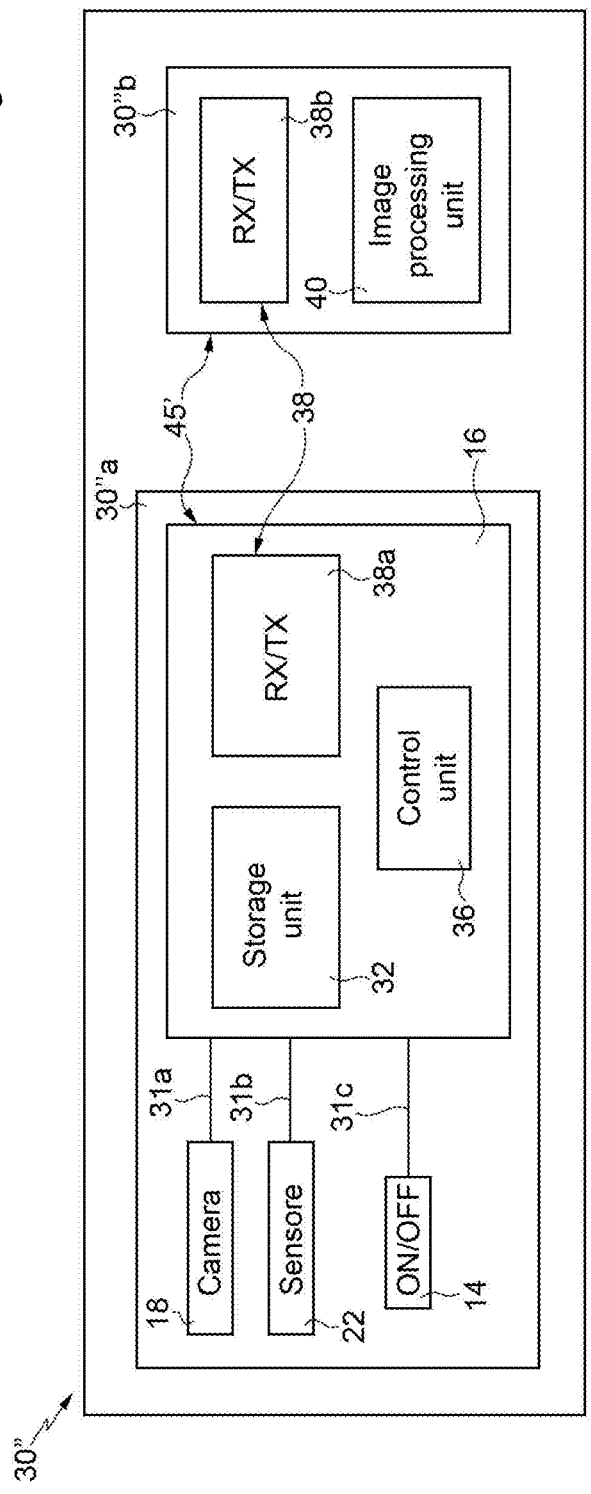
FIG. 3 schematically shows a different embodiment of the evaluation system.

Referring to FIG. 3, the evaluation system according to a different embodiment of the present invention is shown schematically (evaluation system 30"), wherein the evaluation system 50 is performed remotely (outside the slaughtering plant 1). In particular, the evaluation system 30" includes a first portion 30"a and a second portion 30"b of the evaluation system 30". The first portion 30"a of the evaluation system 30" includes the evaluation system components 30" which are inside (for example, housed in) the slaughtering plant 1, while the second portion 30"b of the evaluation system 30" includes the evaluation system components 30" which are outside the slaughtering plant 1 (for example, housed in a different facility than the slaughtering plant 1). In detail, the first portion 30"a of the evaluation system 30" comprises the control device 16, the camera 18, the sensor 22, and the on/off button 14, similarly to the embodiment described in FIG. 2. The control device 16 comprises: the control unit 36; the storage unit 32; and a first communication unit 38a operatively coupled to the control unit 36. Instead, the second portion 30"b of the evaluation system 30" comprises a second image processing unit 40 (similar to the first image processing unit 34 and located outside the slaughtering plant 1, for example housed, placed in, a different city or geographical area with respect to the slaughtering plant 1) and a second communication unit 38b operatively coupled to the second image processing unit 40. The first and second communication units 38a, 38b establish in use an electromagnetic communication to each other (such as wireless connection according to transmission/reception communication protocols of a known kind, such as Local Area Network, LAN, or Wide Area Network, WAN) or Internet, and are therefore operatively connected to each other to form a communication unit 38 (which therefore connects the first portion 30"a of the evaluation system 30" and the second portion 30"b of the evaluation system 30"). The second image processing unit 40 is therefore operatively connected to the control unit 36 through the communication unit 38 and performs, in use, the evaluation method 50 remotely, as better described below. In the present embodiment, the evaluation device 45" includes the control device 16 and the second portion 30"b of the evaluation system 30".

Figure 4:
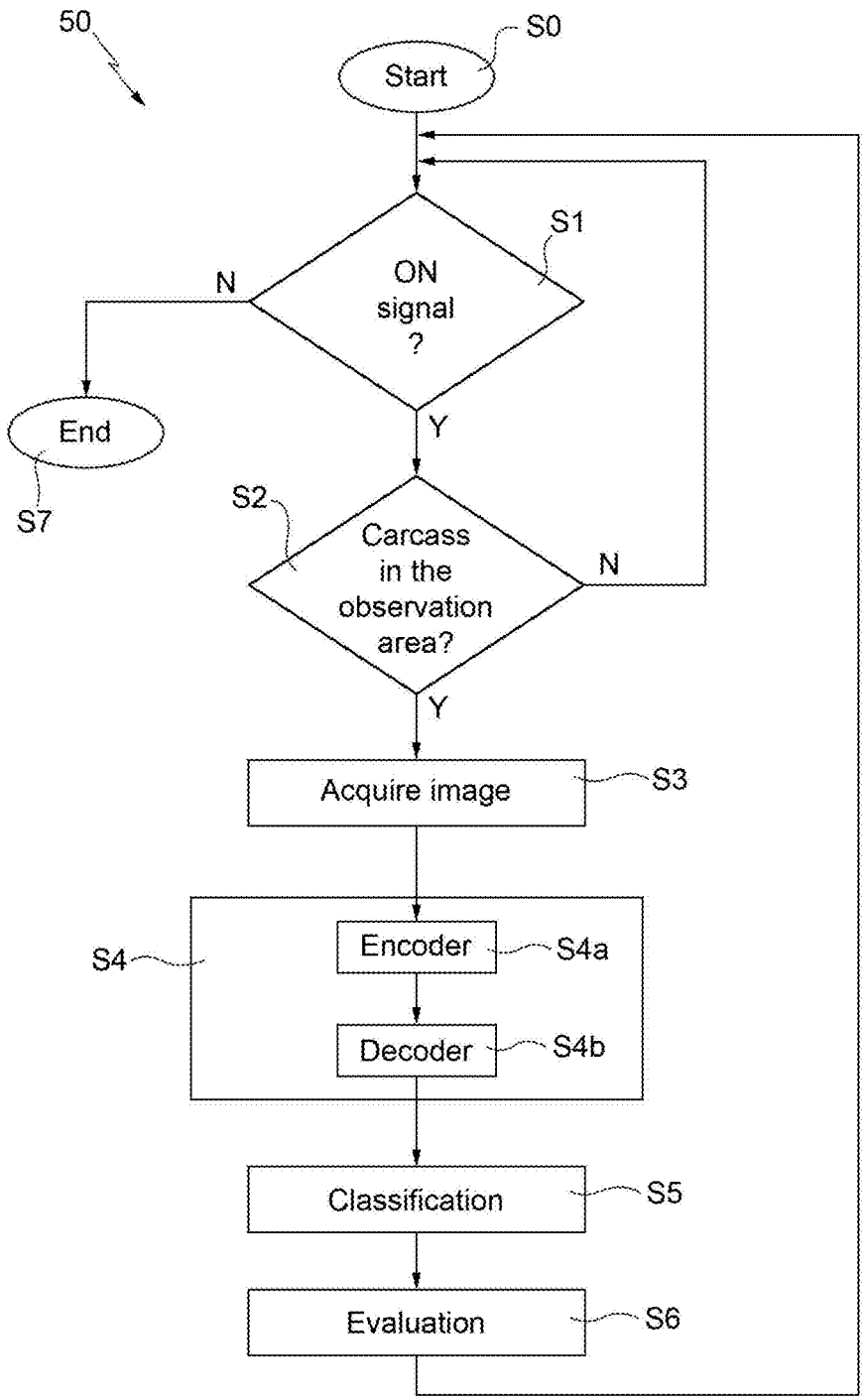
FIG. 4 is a block diagram illustrating an evaluation method which can be performed through the evaluation system of FIGS. 2, 3 according to an embodiment of the present invention.
Figure 5:
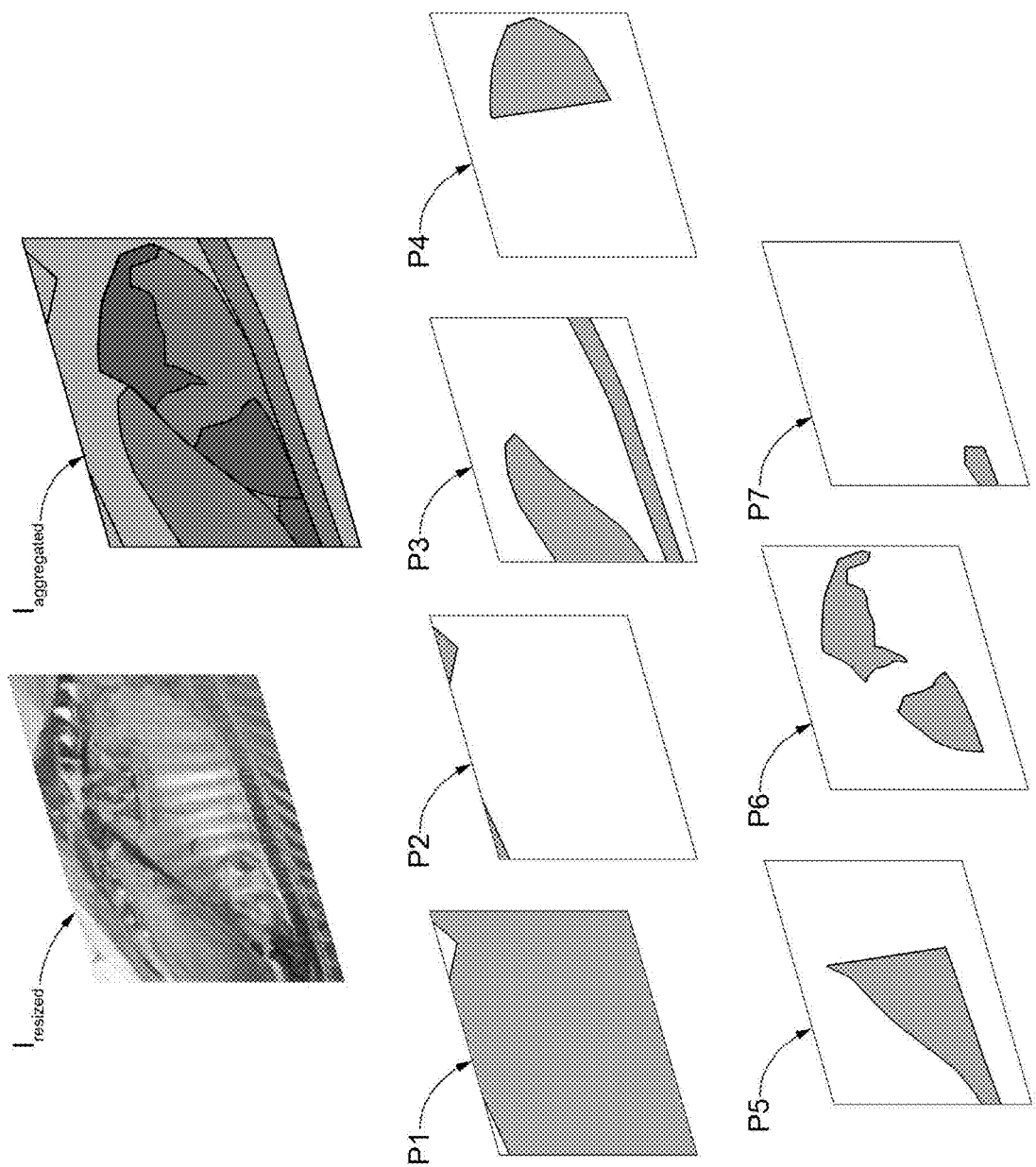
FIG. 5 schematically shows images obtained by implementing the evaluation method of FIG. 4, according to an embodiment of the present invention.

Referring to FIG. 4, the evaluation method 50 is now described, which allows, in use and in an iterative way: verifying, through the image acquisition device 8, 22, the presence of the carcass 10 in the observation area 20; if the presence of the carcass 10 in the observation area 20 is verified, acquiring, through the image acquisition device 18, 22, the image of a carcass 10 which is moved and passes through the observation area 20; processing the image through Machine Learning methods (in particular through Deep Learning methods, by way of one or more neural networks) generating a plurality of processed images (each one indicative of a respective section of the image and therefore of the carcass 10, and referred to as P in FIG. 5) among which a lesion image (P6 in FIG. 5), which represents lesioned portions (hereinafter also called lesions) of the carcass 10, and a number of processed images (P4 and P5 in FIG. 5), each of which represents a corresponding non-lesioned anatomical area of the animal (hereinafter also referred to as anatomical area); for each of the lesioned portions and for each of said non-lesioned anatomical areas, determining a corresponding quantity indicative of the probability that said lesioned portion corresponds to said non-lesioned anatomical area; and determining a score indicative of the health state of the carcass 10, depending on the quantities determined. The evaluation method 50 is described by way of example referring to the detection of pleurites, although it can be of course extended to the person skilled in the art to different diseases, as better described below.

As known, the Deep Learning methods are extremely effective in carrying out image analysis and classification tasks, in some cases exceeding human performance in carrying out certain tasks (for example, "face recognition"). The major limit in achieving this performance is related to the need to train the neural network by providing a significant amount of data, in the order of several thousand images for each task that it has to learn to carry out. Such amount of data aims at ensuring a satisfactory generalization level, the latter measurable by proposing to the model a set of examples never observed previously and verifying the performance of the neural network on such set.

Referring to FIG. 4, the evaluation method 50 starts at a step S0 with the acquisition by the control unit 36 of a start signal through the on/off button 14. The on/off button 14 is brought, by an operator (for example, present in the slaughtering plant 1 and in charge of supervising and/or performing the slaughtering activities) from a first position ("OFF state", wherein the evaluation method 50 is not active and no controls on the carcass 10 are performed) to a second position ("ON state", wherein the evaluation method 50 is active and the control of the carcass 10 is performed) moved with respect to the first position. The control unit 36 acquires through the on/off button 14 the start signal when the on/off button 14 is in the second position, and an end signal when the on/off button 14 is in the first position.

In a step S1, following the step S0, it is verified if the on/off button 14 is in the second position (i.e., if the control unit 36 acquires the start signal). If the on/off button 14 is not in the second position (output "N" from the step S1), the evaluation method 50 ends with a step S7. Instead, if the on/off button 14 is in the second position (output "S" from the step S1), the evaluation method 50 proceeds to a step S2.

In the step S2, following the step S1 through the output "S", it is verified through the control unit 36 and the sensor 22 if the carcass 10 is in the observation area 20. By way of example, according to an embodiment, the sensor 22 is a photocell including a photodiode (not shown and, for example, attached to the support 19 and operatively coupled to the control unit 36) and a photodetector (not shown and, for example, attached to the second side wall 2b at the observation area 20 and operatively coupled to the control unit 36), mutually arranged along a photocell path so that the photodetector detects, in the absence of the carcass 10, a radiation emitted by the photodiode. When the carcass 10 passes in the observation area 20, it is interposed between the photodetector and the photodiode along the photocell path, limiting or interrupting the radiation emitted by the photodiode which is received by the photodetector, and therefore causing a modification (for example, a reduction) of the output current from the photodetector compared to the output current from the photodetector in the absence of the carcass 10. The carcass 10 is therefore detected in the observation area 20 by comparing, through the control unit 36, the modification of the output current from the photodetector with a current threshold (for example, the carcass 10 is present when the modification of the output current from the photodetector is greater than the current threshold). If the carcass 10 is not present in the observation area 20 (output "N" of the step S2), it is verified again if the on/off button 14 is in the second position (step S1). Instead, if the carcass 10 is present in the observation area 20 (output "S" of the step S2), it proceeds to a step S3.

In the step S3, following the step S2 through the output "S", the control unit 36 and the camera 18 acquire the image of the observation area 20 (which therefore shows the carcass 10). According to an embodiment, the observation area 20 is a region of the second side wall 2b having a polygonal shape (for example, a rectangular shape with minor sides in contact with a ceiling edge 7 and a floor edge 8, respectively, and greater sides mutually spaced apart by a distance suited to allow the observation area 20 to include the whole carcass 10, and therefore for example mutually spaced apart by about 1-2 m). The acquired image shows the observation area 20 (and therefore the carcass 10), and can be acquired both in greyscale and in RGB scale.

In a step S4, following the step S3, the acquired image is processed through the Deep Learning methods by the first or second image processing unit 34, 40 (referring to the embodiment of FIG. 2 or FIG. 3, respectively). The structure and characteristics of the neural network implemented in the step S4 are better described below. The neural network receives at the input the image acquired by the camera 18 and generates the processed images P at the output. In the embodiment described by way of example, the neural network generates seven processed images P at the output.

In a step S5, following the step S4, the processed images P are classified, through at least one classifier and as better described below, by the first or second image processing unit 34, 40 (referring to the embodiment of FIG. 2 or FIG. 3, respectively), determining the quantities indicative of the probability that the lesioned portions correspond to the non-lesioned anatomical areas. In particular, the non-lesioned anatomical areas are anatomical areas of the generic animal considered (in the embodiment described by way of example, the pig) when it is not affected by diseases. In this case, the first or second image processing unit 34; 40 generates the processed image which represents a corresponding non-lesioned anatomical area of the animal by reconstructing the shapes of the area on a statistical basis considering the images of carcasses given as an input to the neural network.

In a step S6, following the step S5, the score (and therefore the health state of the carcass 10) is determined by means of the first or second image processing unit 34, 40 (referred to the embodiment of FIG. 2 and FIG. 3, respectively) depending on the quantities determined in the step S5. In particular, the health state of the carcass 10 is associated with the score determined by verifying if the determined score and a reference score mutually satisfy a first predefined relationship. In particular, if the score is lower than, or equal to, the reference score (for example, equal to 0 referring to the embodiments described below on SPES and PEPP methods), the carcass 10 is evaluated as healthy (positive health state), if, instead, the score is higher than such reference score, the carcass 10 is evaluated as sick (negative health state). In the step S6, the score determination and the health state evaluation of the carcass 10 are performed by the control unit 36 after acquiring, by the first or second image processing unit 34, 40, the quantities (generated in the step S5) indicative of the probability that the lesioned portions correspond to the non-lesioned anatomical areas. Optionally, the health state of the carcass 10 is shown to the operator through a message (or notification, or light or acoustic signal, etc.) by means of a signaling device (not shown, such as a screen, or an LED, or headphones, etc.) operatively coupled to the control device 16 and the control unit 36. In addition or alternatively to such message, the carcass health state datum 10 is stored in the storage unit 32 and/or in a platform shared in the cloud, and is accessible to the operator and/or to all the stakeholders of the field in a known manner (for example, by consulting the shared platform, or by connecting to the storage unit 32).

After the step S6, a new verification of the position of the on/off button 14 follows (step S1).

The structure of the neural network implemented in the step S4 is now described.

The neural network includes a coding structure (hereinafter called "encoder", and referred to as step S4a in FIG. 4) and a decoding structure (hereinafter called "decoder", and referred to as a step S4b in FIG. 4). The decoder is sequential to the encoder (the step S4b follows the step S4a, and both the step S4a and the step S4b are included in the step S4) for forming a pipeline structure. The encoder has the task of extracting a plurality of characteristics (hereinafter, "features") from the acquired image, which are located as input of the decoder in order to generate the processed images P.

Referring to the step S4a in FIG. 4, the acquired image is resized obtaining a resized image (shown in FIG. 5 with the reference number $I_{resized}$). In particular, a first dimension (in the embodiment described by way of example, the width) of the resized image $I_{resized}$ has a predefined value (for example, equal to 400 pixels), while a second dimension (in the embodiment described by way of example, the height) of the resized image $I_{resized}$ has a value calculated such to preserve, in the resized image $I_{resized}$, the proportions of the acquired image. In the example of the image acquired in HD (therefore having dimensions 1920×1080×3, considering the RGB scale image with three channels), the resized image $I_{resized}$ has dimensions 400×225×3.

The encoder input (and therefore of the neural network) is therefore the resized image, in the form of a matrix having dimensions 224×224×3. No specific alignment processes of any kind are necessary, since the network is trained by utilizing various Data Augmentation techniques, as better described below. The encoder includes a neural network architecture, Resnet34 (consisting of 34 blocks of convolutional layers) known in literature (see for example the article "Deep Residual Learning for Image Recognition", by K. He et al., 2015) and therefore not further described. These layers act as filters on the respective input by identifying, moving from the encoder input to the encoder output (i.e., towards the decoder), features which are increasingly significant for the task to be carried out. The first layers of the encoder (i.e., the layers closest to the input rather than the output of the encoder) have the task of extracting low-level structures such as sides and angles, while the last layers of the encoder (i.e., the layers closest to the output rather than the input of the encoder) identify more abstract structures such as geometric shapes and/or visual structures. The encoder output is the plurality of features having a very reduced spatial dimension compared to the encoder input. In particular, considering the resized image $I_{resized}$ as the encoder input, the encoder output (i.e., the plurality of features) has dimensions 50×30×512 (where 512 is the number of channels considered). In particular, the output corresponds to a matrix having a second predefined spatial dimension (in the embodiment described by way of example, equal to 28×28×512). The spatial dimension of the output is therefore reduced by a reduction factor (in the embodiment described by way of example, equal to 8) compared to the spatial dimension of the encoder input. Furthermore, the encoder is initialized with the weights resulting from the training of the encoder on a classification dataset of a known kind and including natural images (in detail, ImageNet dataset). This is a common practice that allows increasing the generalization ability of the encoder architecture and reducing the training time required.

Referring to the step S4b in FIG. 4, the decoder receives the plurality of features at the input (encoder output) and makes use of a known technique, the transposed convolution, for enlarging the features dimensionally generating the processed images P, at the output from the decoder, having the same dimensions as the resized image (encoder input). In particular, the decoder has a convolution-based structure, transposed with respect to the encoder structure. Furthermore, there are skip connections (of a known kind) between encoder and decoder which allow transferring the information in a more immediate way during the training step. In other words, layers of the encoder and decoder corresponding to each other (for example, the N-th layer of the encoder calculated starting from the input and going towards the output of the encoder, and the N-th layer of the encoder calculated starting from the output and going towards the input of the decoder) are mutually connected through channels (skip connection) by which the information is exchanged. This technique is widely known and utilized in the state of the art to allow also the features extracted from the first layers of the encoder to contribute directly to the decoder output without having to pass through both the encoder and decoder. The decoder output (and therefore the output of the neural network) are the processed images P (a processed image P for each section of interest of the carcass 10, in particular for the lesions or for each anatomical area of interest of the carcass 10). Referring to FIG. 5, the processed images P are identified by the lesions or respective anatomical areas and, in the embodiment described by way of example, are: a carcass image P1 (indicative of the carcass 10), a background image P2 (indicative of a background of the resized image), an image of the spine and diaphragm P3 (indicative of spine and diaphragm of the carcass 10), an image of the first portion of the hemithorax P4 (indicative of a first portion of the hemithorax of the carcass 10), an image of a second portion of the hemithorax P5 (indicative of a second portion of the same hemithorax of the carcass 10), the lesion image P6 (indicative of the shape, dimension and position of the lesions of the carcass 10, indicative of the disease of the food-producing animal), and an artifact image P7 (indicative of possible artifacts in the carcass 10 due to factors such as cuts or perforations of the carcass 10 performed mistakenly by an operator in charge of cleaning the carcass 10, or to portions of tissue not removed from the carcass 10). In particular, such first portion of the hemithorax extends from a first intercostal space to a fifth intercostal space, while the second portion of the hemithorax extends to all the remaining intercostal spaces located caudally (i.e., it extends from the fifth intercostal space to the fifteenth or sixteenth rib depending on the race). In a preferred embodiment, the processed images P considered are three, and they are in particular the lesion image P6, the image of the first portion of hemithorax P4, and the image of the second portion of hemithorax P5. Each processed image P is a two-dimensional matrix whose elements have respective values in a predefined range (in the embodiment described by way of example, which varies between 0 and 1, with 0 and 1 included). Every element of each matrix having a value higher than a predefined threshold (for example, equal to 0.5) is considered to be part of the anatomical area of the respective processed image P, while every element of each matrix having a value lower than such predefined threshold is considered as not part of the anatomical area of the respective processed image P. The decoder output is therefore a matrix having a third predefined spatial dimension (in the embodiment described by way of example, equal to 224×224×7, where seven is the number considering the lesion image P6 and the anatomical areas of interest). The processed images P are therefore independent of each other, and this allows reconstructing the complete anatomical area as described below and in particular, in the event of occlusions (lesion or artifact) on the first and/or second portion of the hemithorax, reconstructing such hemithorax as a whole.

The classification, implemented in the step S5 by the classifier, of the processed images P at the output of the neural network is now described.

Although the neural network allows, by the processed images P, visually inspecting the result of the analysis of the carcass 10 and, in detail, the presence/absence of lesions of veterinary interest, to obtain an aggregated datum it is necessary to generate a score (based on one of the classification methods commonly known and currently in force better described below). It is therefore necessary to identify the class to which the analyzed carcass 10 belongs from a set of possible classes.

In the embodiment described by way of example, the processed images P utilized in such classification are: the image of the first portion of hemithorax P4, the image of the second portion of hemithorax P5, and the lesion image P6. The classification performed in the step S5 includes the steps of: identifying the possible lesions in the lesion image P6; comparing the possible lesions identified to the first and second portions of the hemithorax, in a known manner, through the neural network; and generating, based on the comparison made between the lesions and the first and second portions of the hemithorax, the at least one quantity of probabilistic value (hereinafter also referred to as probabilistic quantity). In particular, the classifier identifies each lesion, if any, by processing the lesion image P6 by the known connected components technique. The connected components technique allows identifying connected regions (lesions of the carcass 10) of the lesion image P6 by comparing the value of each pixel of the lesion image P6 (i.e., of each element of the matrix corresponding to the lesion image P6) with the predefined threshold (for example, equal to 0.5). Each element of the lesion image P6 having a value higher than the predefined threshold is considered to be part of a lesion, while each element of the lesion image P6 having a value lower than such predefined threshold is considered as not being part of any lesions. The pixels having respective values higher than the predefined threshold are then grouped into a number of pixel groups (each pixel group including pixels connected to each other). Subsequently, each lesion is compared to the first and second portions of the hemithorax for identifying overlaps. It is not necessary to isolate connected components in the image of first portion of hemithorax P4 and in the image of second portion of hemithorax P5 respectively (corresponding to the first and second portions of the hemithorax, respectively), since the neural network is trained to identify automatically, in a known manner, the first and second portions of the hemithorax in the image of first portion of hemithorax P4 and in the image of second portion of hemithorax P5 respectively. Given the mutual overlappability of the processed images P (see an aggregated image $I_{aggregated}$ in FIG. 5, obtained by graphically overlapping some processed images P), the lesion image P6 is compared to the image of first portion of hemithorax P4 and the image of second portion of hemithorax P5 for verifying, for each lesion, if such lesion corresponds (for example, is located and/or overlapped) to the first and/or second portion of hemithorax. In particular, for each lesion, by overlapping such lesion with the first portion of hemithorax and/or the second portion of hemithorax, an intersection area $A_{intersection,k}$ of the lesion with the first portion of hemithorax and/or the second portion of hemithorax is calculated (where the subscript k has a first or a second value, for example 1 or 2, and identifies the overlap with the first or second portion of the hemithorax, respectively). For each lesion and for each anatomical area, the probabilistic quantity is generated depending on the intersection area $A_{intersection,k}$ (for example, the probabilistic quantity is equal to the intersection area $A_{intersection,k}$, normalized with respect to an area of the lesion considered).

In the step S6, the following actions are performed: for each lesioned portion in the lesion image P6, the respective overlap area $A_{intersection,k}$ is compared with an overlap threshold $T_{intersection,k}$; the lesioned portions whose overlap area $A_{intersection,k}$ respects a second predefined relationship with the overlap threshold $T_{intersection,k}$ are identified as selected lesioned portions; and the score is determined based on the selected lesioned portions. In particular, referring to the second predefined relationship, for each lesion, if the intersection area $A_{intersection,k}$ greater than, is or equal to, the intersection threshold $T_{intersection,k}$, the presence of the lesion considered in the k-th portion of the hemithorax occurs (first portion of hemithorax if k=1 and second portion of hemithorax if k=2), and therefore such lesion is included among the selected lesioned portions; instead, if the intersection area $A_{intersection,k}$ is less than the intersection threshold $T_{intersection,k}$, the absence of the lesion considered in the k-th portion of the hemithorax occurs, and therefore such lesion is not included among the selected lesioned portions. The intersection threshold $T_{intersection,k}$ is calculated, for the k-th portion of the hemithorax, according to the following expression: $T_{intersection,k}=a \cdot A_{intersection,k}$, where a is a multiplication factor ranging between 0 and 1 (0 and 1 excluded). The score is assigned to the carcass 10 based on known evaluation grids, depending on the selected lesioned portions (in particular, on the number of selected lesioned portions).

Figure 6:
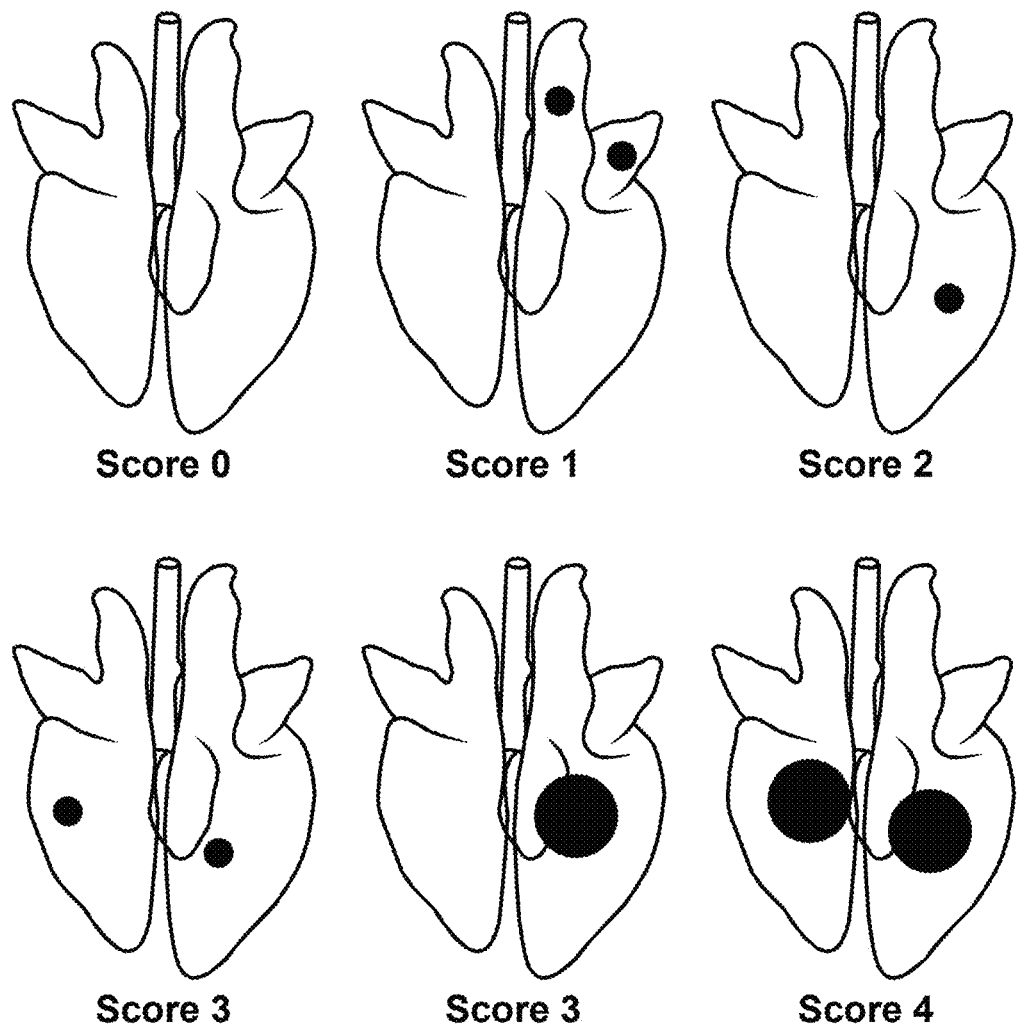
FIG. 6 schematically shows lesions on an organ of a food-producing animal, with respective scores based on a known kind of evaluation grid according to an embodiment of the present invention.

In detail, in an embodiment of the present invention, the classifier implements a modified version of the PEPP method (Pleurisy Evaluation on the Parietal Pleura). The PEPP method is based on the detection and quantification of pleurites on the parietal pleura, i.e., the membrane lining the internal surface of the chest wall. The modified PEPP method provides for the parietal pleura to be divided into two easily identifiable areas: a first area extending from the first to the fifth intercostal space (thus corresponding to the first portion of the hemithorax); and a second area extending to all the remaining intercostal spaces located caudally (thus corresponding to the second portion of the hemithorax). The modified PEPP method gives in particular: 0 points in the absence of lesions; 1 point to the pleurites affecting the first five intercostal spaces (the first portion of the hemithorax); 2 points to the pleurites involving the remaining intercostal spaces (the second portion of the hemithorax); and 3 points to the pleurites affecting both the first portion of hemithorax and the second portion of hemithorax. The total score of the hemithorax results from the sum of the scores of each single area of the hemithorax itself and therefore varies from 0 to 3. In general, the PEPP system can be utilized as an alternative to another scoring system for pleurites, the so-called "SPES grid" (Slaughterhouse Pleuritis Evaluation System). This system offers at least two advantages: (1) it is extremely simple and quick to perform; and (2) it clearly discerns ventro-cranial from dorso-caudal lesions. The latter are closely linked to the *Actinobacillus pleuropneumoniae* infection, one of the causative agents of porcine pleuropneumonia. The SPES grid quantifies the pleurites of the visceral pleura (the serous membrane lining the lung), giving each pig a score ranging from 0 to 4. Instead, on an entire batch of pigs, the SPES grid provides two results: (1) an average value, also called "SPES index", which generally describes the presence of pleurites in the group of animals under examination; and (2) the *Actinobacillus pleuropneumoniae* index (APPI) which provides specific information on the prevalence and severity of the dorso-caudal pleurites, i.e., those directly related to the *Actinobacillus pleuropneumoniae* infection. Referring to FIG. 6 (Luppi and Merialdi, 2013), examples of pleural lesions on the lungs of pigs at the slaughterhouse classified according to the SPES grid are shown schematically. In detail, score 0 is assigned in the absence of lesions ("Score 0" in FIG. 6). Score 1 is assigned in the event of ventro-cranial and/or interlobar pleural lesions ("Score 1" in FIG. 6). Score 2 is assigned in the event of focal, unilateral lesions affecting the diaphragmatic lobes ("Score 2" in FIG. 6). Score 3 is assigned ("Score 3" in FIG. 6) in the event of bilateral lesions affecting both diaphragmatic lobes, or in the event of extended unilateral lesions (for example, lesions of more than 30% of the diaphragmatic lobe). Score 4 is assigned in the event of extended, bilateral lesions affecting the diaphragmatic lobes ("Score 4" in FIG. 6). As expected, considering that pleuritis usually affects both pleural sheets (visceral and parietal), the scores achieved with the SPES grid and PEPP method proved to be strongly correlated. Furthermore, it has been shown that the modified PEPP method has the advantage to be effectively applied on remote digital images.

The neural network training implemented in the step S4 is described here.

A consolidated approach for neural network training is the supervised one: during training, training images previously noted by certified operators skilled in the field are submitted to the neural network (therefore, training images with the respective segmentation, i.e., with the respective processed images P obtained by such operators). The training and neural network success lies in the ability of the neural network to learn the same segmentation criterion utilized by the skilled operator. Once the training is successfully completed, the model is able to assist, or replace (partially or totally), the human intervention on the lesion segmentation of the carcass 10. In particular, training begins by acquiring, as an input, the training dataset by the neural network (including approximately 10,000 training images for each task to be learned by the neural network, and respective segmentations). Before entering the neural network, such dataset was processed according to Data Augmentation techniques. This term identifies a set of techniques aimed at improving the generalization ability of the network (i.e., the ability to adapt to new data never examined during the training step) by operations on the dataset itself. In particular, the training images of the dataset are processed according to at least one of the following techniques: rotation of the training image by an angle randomly included in the ±15-degree range with respect to a reference axis; vertical or horizontal mirroring (each with a probability equal to 0.5); shifting in the ±15% range in four different directions; scaling in the ±10% range with respect to the original dimensions; and hue variation (for example in a relative range equal to approximately ±0.1), saturation (for example in a relative range equal to approximately ±0.5) and brightness (for example in a relative range equal to approximately ±0.5). The first 4 points of such list make the network solid at different image acquisition distances and positions, while the last point reduces sensitivity to different light conditions. Training requires the availability of important hardware resources (for example, equipped with different GPUs) and capable of processing data in an optimized way for training neural networks. At each iteration of the training step, the output of the neural network is compared to the corresponding segmentation datum (i.e., to the corresponding processed image P) noted by the experts. A loss function (such as one known as "Binary Cross Entropy, BCE, loss function") is utilized to minimize the difference between the neural network output and the processed images P. Each processed image P is individually compared to the correspondent one noted by the experts. The areas obstructed by further anatomical parts are also compared by forcing the network to reconstruct these structures even if not directly visible in the input dataset image. The training ends upon reaching a predetermined number of training iterations (for example, when all available images have been randomly submitted to the neural network 10 times), or when the difference between the neural network output and the noted belonging classes is lower than or equal to a training threshold.

From an examination of the features of the evaluation method, the related evaluation device and the related evaluation system realized according to the present invention, the advantages which they allow obtaining are evident.

In particular, the automation obtained through the present invention is of great value for all the stakeholders in the field, such as butchers, farmers, veterinarians, health authorities and governments, consumers, and feed and pharmaceutical companies. Allowing a systematic examination of all the animals at the slaughterhouse would influence positively the management of farmed animals and would allow for an even more precise control over their health and well-being.

In fact, the present invention is capable of automating, by employing Artificial Intelligence technologies, the acquisition and classification process (through the scoring shared by the scientific community or defined by the legislation) of the lesions present in the carcasses 10 (half carcasses and/or organs of slaughtered animals), starting from non-pre-processed images. This is made possible by implementing neural networks and Deep Learning techniques for analyzing the acquired images and assigning them a score (of lesion seriousness). Deep Learning-based approaches do not require any measurements or parameters calculated instrumentally or manually for assigning scores. In fact, the scoring occurs directly from the image acquired and analyzed by the neural network, as previously described.

Such neural network models are first trained with images previously noted and classified by experts in the field; after which, in accordance with the supervised Machine Learning paradigm, the neural networks are capable of replicating the notation and classification process with reasonable accuracy in a completely automatic way. One of the main advantages of the systems realized with Artificial Intelligence-based technologies is that as the available data employed for the training steps increase, the performance of such systems keep on improving. In particular, it has been verified that the evaluation method 50 allows reaching an accuracy in evaluating pleurites in pigs equal to approximately 0.86.

The present invention can be employed in the slaughtering chain for providing a real-time systematic diagnosis (identification and scoring) of all half carcasses and/or organs which is, at the same time, efficient, standardized, and economically more advantageous than the current evaluation systems performed by an operator.

The automation of the process would allow a significant reduction in costs and, above all, acquiring a significant amount of data in real time, useful for providing feedback to the company cattle farmer and veterinarian, as well as for classifying the companies by risk categories (for example, referring to an application called "ClassyFarm" aimed at facilitating the collection of data for classifying companies according to different types of risk). All stakeholders would have access to the data, statistics, and results in a simple and easy to understand manner according to their respective access rights and privileges.

In particular, the following advantages of the present invention are identified:
- possibility to analyze, without interruption and at any time, the carcasses and/or organs and/or half carcasses on an automated line. This makes possible a massive acquisition and analysis of data which otherwise are often lost;
- the evaluations of the lesions on organs and/or half carcasses are carried out by assigning a score so as to be able to measure the seriousness and/or extent thereof in a standardized way, and therefore to make the data comparable both between batches from the same stock farm and from other stock farms;
- the scoring of the lesions would allow a systematic collection and analysis of the slaughtering data at reduced costs even to those slaughterhouses which for logistical and/or economic and/or organizational reasons cannot always have access to the skills/resources necessary to carry out these evaluations;
- a systematic examination of the slaughtered animals would positively influence the management choices in the stock farms and would allow to exercise an accurate control on their health state and well-being;
- the evaluation process of the lesions and carcasses at the slaughterhouse would become faster, simpler, cheaper, standardized, and accurate;
- it introduces the possibility of carrying out a double verification. The acquired images could be re-analyzed remotely by certified evaluators, so as to guarantee greater control also for the protection of consumers;
- the massive evaluation of the presence of lesions at the slaughterhouse can allow the creation of indicators of the animals' well-being and allow the implementation of possible corrective measures for solving problems during breeding; and
- the collection of accurate health data on all slaughtered animals can provide important indications on the health state of a certain stock farm and therefore allow to follow the progress thereof over time. This is essential for monitoring the correct use of antimicrobials.

Finally, it is evident that modifications and variations to the evaluation method, the related evaluation device and the related evaluation system described and illustrated here can be made without departing from the protective scope of the present invention, as defined in the attached claims.

In particular, the present invention can be applied to a plurality of animals (in particular, food-producing animals such as cattle, sheep, goats, horses, and chickens) and allows detecting a plurality of diseases through modifications which are obvious to the person skilled in the art with respect to what previously described. By way of example, some examples of such diseases detectable by means of the present invention are reported here.

In an embodiment, the present invention is utilized for detecting sarcoptic mange. Sarcoptic mange, originated by the mite *Sarcoptes scabiei*, represents one of the parasitic diseases of considerable economic impact in modern pig breeding. The disease is widespread in pig breeding and can cause significant economic losses due to reduced growth, worsening of the food conversion index, increase in mortality of piglets in suckling phase due to crushing phenomena. At the slaughterhouse, it is possible to view and quantify the skin papules resulting from the *Sarcoptes scabiei* infection. Such lesions are particularly evident after the passage of the carcass into the scalding tank and after removing the bristles. Currently, one of the most commonly used evaluation systems gives the following scores: 0 points in the absence of lesions; 1 point with lesions localized in the head, belly and glutes; 2 points for generalized moderate-intensity lesions; and 3 points with more severe generalized lesions (Luppi A., Merialdi G., 2013. In Le patologie del maiale, pp 199-216, Milan: Le Point Veterinaire Italie). In the present embodiment, at least 3,000 representative images (i.e., with a balanced number of absence/presence of lesions of interest) of the external side of the half carcass are acquired. Referring to the already introduced method, the number of processed images P is equal to four, and they correspond to the background, half carcass, lesion, and artifact, respectively. The score of the lesion is given according to the presence of the lesion itself. The neural network works as previously described, while the classifier can be simplified to a threshold adapted for quantifying the presence/absence of lesions.

In a different embodiment, the present invention is utilized for detecting parasitic hepatitis. Such infection, caused by the nematode *Ascaris suum*, is a major parasitic disease in intensive pig farms. At the slaughterhouse, it is possible to indirectly estimate the economic impact of ascariasis according to the severity of parasitic hepatitis caused by the larval forms of *Ascaris suum* during their migration within the host. Maw-worms liver lesions are easily recognizable (so-called "milk spots" on the liver). Currently, there are two main evaluation methods, both based on milk spot counting. The first method is mainly employed in the United States and provides for assigning the score 1 in case the number of lesions detected is lower than 10, and the score 2 in case the number of lesions detected is higher than or equal to 10. The second method, mainly adopted in Europe, involves giving the following scores: 1 point up to 4 milk spots detected; 2 points from 5 to 15 milk spots detected; and 3 points for more than 15 milk spots (Luppi and Merialdi, 2013). By their very nature, *Ascaris suum* liver lesions are suitable for being scored remotely on digital images. In the present embodiment, at least 3,000 representative images (i.e., with a balanced number of absence/presence of lesions of interest) of the liver of the animal are acquired. Referring to the already introduced method, the number of processed images P is equal to four, and they correspond to the background, liver, lesion, and artifact, respectively. The score of the lesion is given according to the presence of the lesion itself. The neural network works as previously described, while the classifier can be simplified to the application of the algorithm of connected components in order to count the number of lesions.

In a further embodiment, the present invention is utilized for detecting pneumonia. In slaughtered pigs, it is possible to evaluate and quantify the presence of lesions caused by enzootic pneumonia, resulting from *Mycoplasma hyopneumoniae* infection, often led to complications by further secondary bacterial infections. Enzootic pneumonia still represents one of the most common and most impactful diseases in pig farm. Enzootic pneumonia has a chronic course and the lesions (typically bilateral, symmetrical and localized at the cranio-ventral portions of the lungs) are usually still visible at the slaughterhouse, albeit with some variations based on the slaughtering age. Over the years, several systems have been developed for scoring lung lesions. In most of the advanced production companies, the so-called "Madec grid" has been largely employed, assigning a score ranging from 0 to 4 to each of the 7 lung lobes in the following way: 0 points in the absence of lesions; 1 point in case pneumonia involves less than 25% of the lobe extension; 2 points in case pneumonia involves 26-50% of the lobe extension; 3 points in case pneumonia involves 51-75% of the lobe extension; and 4 points in case pneumonia involves 76-100% of the lobe extension (Luppi and Merialdi, 2013). The scoring of pneumonia is relatively simple, although it shows a certain margin of subjectivity and can be made more complex by the presence of slaughtering artifacts (e.g., *inspiratio sanguinis*). The present invention, through the correct identification of lesions and artifacts, can therefore efficiently detect such disease. In the present embodiment, at least 3,000 representative images (i.e., with a balanced number of absence/presence of lesions of interest) of the lungs of the animal are acquired. Referring to the already introduced method, the number of processed images P is equal to eight, and they correspond to the background, lung, lesion, artifact, and four lobes of interest, respectively. The score of the lesion is given according to the presence, localization and extent of the individual lesions. The neural network works as previously described, while the classifier is adapted to identify the overlap and extension between each lesion and the lobes.

In an embodiment of the present invention, the actions performed, in the embodiment of FIG. 3, by the second image processing unit 40 are performed on the cloud, in an evident way to the person skilled in the art. In particular, once analyzed and classified, the acquired images are stored on a proprietary platform (shared platform) which makes both the individual images and the aggregate and processed datum accessible (for example, processed images and the carcass's score) by specific analysis means. Where required, this allows the operator in charge to evaluate the carcasses and carry out possible further verifications on the assigned scores and acquired images with parameters off the charts. The operator in charge can thus possibly make a final judgment thanks to the help of the evaluation already obtained by means of the present invention. Thanks to the storage on the cloud, the information collected is easily accessible to all stakeholders (stock farmers, slaughterhouses, veterinarians, health authorities, governments, and pharmaceutical companies), thus allowing a clearer and more objective evaluation of the health state of the investigated animals.

According to an embodiment, the camera 18 and the sensor 22 are replaced by a video camera (not shown and arranged in a similar way to the camera 18). In use, the video camera acquires a video of the observation area 20 and the video frames are used as acquired images to be processed to evaluate the carcass 10. In particular, known tracking systems can be implemented so as to perform the evaluation of each carcass 10 which passes at the observation area 20 only once. In other words, given a set of frames which, through the tracking systems, are associated with the same carcass 10, only a selected frame is chosen in such set of frames to be used as an acquired image to be processed in the steps S4, S5. Optionally, more frames can be joined and/or overlapped, according to known techniques, to generate the acquired image to be processed in the steps S4, S5, with a subsequent improvement in the quality of the acquired image.

According to a different embodiment, the camera 18 is replaced by a video camera (not shown and arranged similarly to the camera 18). In use, the sensor 22 activates the video camera only when the carcass 10 is at the observation area 20, and the video camera records a video (therefore having lesser duration and dimensions than the video described in the previous embodiment) of such carcass 10. The video acquisition stops when the sensor 22 no longer detects the presence of the carcass 10 in the observation area 20. Each acquired video is therefore indicative of, and corresponding to, a respective carcass 10. Similarly to the embodiment previously described, a frame of such video (or the overlap of multiple video frames) is used as an image acquired to perform the steps S4, S5.

According to an embodiment, the sensor 22 is a snap-in sensor (not shown) physically coupled to the slide guide 4 at the observation area 20. In use, the passage of the slide 5 in the slide guide 4 at the sensor 22 mechanically actuates (for example, moves), in a known manner, an actuating element of the sensor 22 which thus detects the presence of the carcass 10 in the observation area 20.

According to a further embodiment, the sensor 22 is a snap-in sensor (not shown) operatively coupled to a scene depth acquisition sensor. Such depth acquisition sensor allows identifying when the single half carcass is centered with respect to the observation area 20. In fact, if the half carcass is in front of the depth acquisition sensor, the average depth value decreases compared to the value recorded in the absence of the half carcass. Through the spatial localization of this minimum point it is therefore possible to acquire a picture of the half carcass which is centered with respect to the observation area 20 (i.e., with respect to the sensor 22).

According to a further embodiment, the classifier implemented in the step S5 of FIG. 4 implements one of the classification algorithms known in literature. In particular, the classifier is a Support Vector Machine (SVM) or Random Forest (RF), or Decision Tree classifier, which receives at the input the processed images P obtained by processing the acquired image, and it is trained, in a known manner, for generating a corresponding score indicative of the health state of the animal.

According to an embodiment, the slaughtering plant 1 houses at least one rotary element (not shown) adapted to rotate the carcass 10 supported by the hook 6 so as to optimize the acquisition of information of the acquired image. In the exemplary case of FIG. 1 related to the detection of pleurites, the carcass 10 present in the observation area 20 must be arranged such that the hemithorax is positioned in front of the camera 18, and the back faces the second lateral wall 2b. This can be done manually (by the operator rotating the carcass 10) or automatically (through the rotary element). The rotary element can be interposed between the slide 5 and the hook 6 to physically connect them to each other. For example, the rotary element includes a rotor, attached to the hook 6, and a stator, attached to the slide 5. In use, the rotor is actuated, in a known manner, to rotate the carcass 10, arranging it such that the hemithorax faces the camera 18.

Furthermore, according to an embodiment, the evaluation method can be applied, with appropriate modifications, to the classification of the carcasses aimed at assigning a corresponding economic and market value.

The invention claimed is:

1. A method for evaluating (50) the health state of an anatomical element (10) of an animal in a slaughtering plant (1), the slaughtering plant (1) being provided with an image acquisition device (18, 22) arranged so as to acquire an image of an observation area (20) of the slaughtering plant (1), the evaluation method (50) comprising the steps of:
    verifying (S2), through the image acquisition device (18, 22), the presence of the anatomical element (10) in the observation area (20);
    if the presence of the anatomical element (10) in the observation area (20) is verified, acquiring (S3), through the image acquisition device (18, 22), the image of the anatomical element (10);
    processing (S4), by an image processing unit (34; 40) operatively coupled to the image acquisition device (18, 22), the image of the anatomical element (10) through deep learning techniques, generating a lesion image (P6), which represents lesioned portions of the anatomical element (10), and a number of processed images (P4, P5), each of which represents a corresponding non-lesioned anatomical area of the animal;
    for each of the lesioned portions and for each of the non-lesioned anatomical areas, determining (S5) a corresponding quantity indicative of the probability that said lesioned portion corresponds to said non-lesioned anatomical area;
    determining (S6) a score indicative of the health state of the anatomical element (10), depending on the determined quantities.

2. The evaluation method according to claim 1, wherein the step of processing (S4) the image of the anatomical element (10) through the deep learning techniques comprises the steps of:
    resizing (S4a) the image generating a resized image ($I_{resized}$) having at least one predefined size;
    processing (S4a) the resized image ($I_{resized}$) through a first portion of a neural network, identifying a plurality of features of the resized image ($I_{resized}$); and
    processing (S4b) the plurality of features of the resized image ($I_{resized}$) through a second portion of the neural network, generating at least the lesion image (P6) and the number of processed images (P4, P5), the second portion of the neural network having a transposed structure with respect to a structure of the first portion of the neural network.

3. The evaluation method according to claim 2, further comprising the steps of:
    processing training images using one or more data augmentation techniques generating a training data set; and
    training the neural network based on the training data set through supervised training by means of a loss function.

4. The evaluation method according to claim 1, wherein the step of determining (S5) each quantity comprises the steps of:
    identifying, through a connected component technique, the number of lesioned portions in the lesion image (P6); and
    comparing the lesioned portions and the non-lesioned anatomical areas to each other.

5. The evaluation method according to claim 4, wherein the step of comparing the number of lesioned portions and the non-lesioned anatomical areas to each other comprises the step of calculating, for each lesioned portion in the lesion image (P6), a respective overlap area ($A_{intersection,k}$) between such lesioned portion and each non-lesioned anatomical area.

6. The evaluation method according to claim 5, wherein the step of determining (S6) the score indicative of the health state of the anatomical element (10) comprises the steps of:
comparing, for each lesioned portion in the lesion image (P6), the respective overlap area ($A_{intersection,k}$) with an overlap threshold ($T_{intersection,k}$);
identifying as selected lesioned portions the lesioned portions whose overlap area ($A_{intersection,k}$) satisfies a predefined relation with the overlap threshold ($T_{intersection,k}$); and
determining the score based on the selected lesioned portions.

7. The evaluation method according to claim 1, the anatomical element (10) being a carcass, the evaluation method being configured to detect pleurites in the carcass, and wherein the step of processing (S4) the image of the carcass through the deep learning techniques comprises the step of generating at least: an image of a first portion of hemithorax (P4), indicative of a first portion of hemithorax of the carcass; an image of a second portion of hemithorax (P5), indicative of a second portion of hemithorax of the carcass; and the lesion image (P6),
the processed image (P4, P5) being the image of the first portion of hemithorax (P4) and/or the image of the second portion of hemithorax (P5).

8. The evaluation method according to claim 1, wherein the step of determining (S5) each quantity comprises the step of processing the lesion image (P6) and the number of processed images (P4, P5) through one of the following classifiers: support vector machine classifier, SVM; random forest classifier, RF; and decision tree classifier.

9. The evaluation method according to claim 1, wherein the step of verifying (S2) the presence of the anatomical element (10) in the observation area (20) comprises the step of detecting the anatomical element (10) through at least one sensor (22) selected from: a photocell, or a sensor based on laser technology, or an acoustic sensor, or a snap-in sensor.

10. The evaluation method according to claim 1, wherein the image acquisition device (18, 22) comprises a video camera, and the step of acquiring (S3) the image of the observation area (20) comprises the step of acquiring, through such video camera, a video of the observation area (20), one or more frames of this video forming the image of the observation area (20).

11. An evaluation device (45'; 45") to evaluate the health status of an anatomical element (10) of an animal in a slaughtering plant (1), the evaluation device (45'; 45") being operatively couplable to an image acquisition device (18, 22) arranged so as to acquire an image of an observation area (20) of the slaughtering plant (1), the evaluation device (45'; 45") comprising a control unit (36) operatively coupled to an image processing unit (34; 40),
wherein the control unit (36) is configured to:
verify, through the image acquisition device (18, 22), the presence of the anatomical element (10) in the observation area (20); and
if the presence of the anatomical element (10) in the observation area (20) is verified, acquire, through the image acquisition device (18, 22), the image of the anatomical element (10),
and wherein the image processing unit (34; 40) is configured to:
process the image of the anatomical element (10) through deep learning techniques, generating a lesion image (P6), which represents lesioned portions of the anatomical element (10), and a number of processed images (P4, P5), each of which represents a corresponding non-lesioned anatomical area of the animal;
for each of the lesioned portions and for each of said non-lesioned anatomical areas, determine a corresponding quantity indicative of the probability that said lesioned portion corresponds to said non-lesioned anatomical area; and
determine a score indicative of the health state of the anatomical element (10), depending on the determined quantities.

12. The evaluation device according to claim 11, wherein the control unit (36) and the image processing unit (34; 40) are mutually coupled electromagnetically or through the Internet.

13. An evaluation system (30'; 30") for evaluating the health state of an anatomical element (10) of an animal in a slaughtering plant (1), the evaluation system (30'; 30") comprising:
the evaluation device (45'; 45"), according to claim 11; and
an image acquisition device (18, 22), operatively coupled to the evaluation device (45'; 45").

* * * * *